US010215998B2

(12) United States Patent
Leonberger et al.

(10) Patent No.: US 10,215,998 B2
(45) Date of Patent: Feb. 26, 2019

(54) OPTICAL IMAGING SYSTEMS WITH MICROLENS ARRAY WITH INTEGRAL STRUCTURE

(71) Applicant: SuRe Optics, Inc., Cambridge, MA (US)

(72) Inventors: Frederick J. Leonberger, Sarasota, FL (US); Jeffrey Farmer, Chelmsford, MA (US); Zong-Long Liau, Belmont, MA (US)

(73) Assignee: Sure Optics, Inc., Cambridge, MA (US)

( * ) Notice: Subject to any disclaimer, the term of this patent is extended or adjusted under 35 U.S.C. 154(b) by 182 days.

(21) Appl. No.: 15/142,224

(22) Filed: Apr. 29, 2016

(65) Prior Publication Data
US 2016/0320628 A1 Nov. 3, 2016

Related U.S. Application Data

(60) Provisional application No. 62/155,603, filed on May 1, 2015.

(51) Int. Cl.
| | | |
|---|---|---|
| *G02B 21/06* | (2006.01) | |
| *G02B 27/58* | (2006.01) | |
| *G02B 21/16* | (2006.01) | |
| *G02B 21/34* | (2006.01) | |
| *G01N 21/03* | (2006.01) | |
| *B01L 3/00* | (2006.01) | |
| *G02B 3/00* | (2006.01) | |
| *G01N 21/64* | (2006.01) | |

(52) U.S. Cl.
CPC ............ *G02B 27/58* (2013.01); *B01L 3/5085* (2013.01); *G01N 21/0303* (2013.01);
(Continued)

(58) Field of Classification Search
CPC .... G02B 21/00; G02B 21/0004; G02B 21/34; G02B 3/0006; G02B 3/0075
(Continued)

(56) References Cited

U.S. PATENT DOCUMENTS

| 6,610,256 B2 | 8/2003 | Schwartz | |
|---|---|---|---|
| 6,683,723 B2 * | 1/2004 | Frosig | G02B 3/0056 359/368 |

(Continued)

FOREIGN PATENT DOCUMENTS

WO 2014142913 A1 9/2014

OTHER PUBLICATIONS

"Notification of Transmittal of the International Search Report and the Written Opinion of the International Searching Authority, or the Declaration" for International Patent Application No. PCT/US2016/030114, dated Aug. 19, 2016, 19 pages, International Searching Authority, Korean Intellectual Property Office, Daejeon, Republic of Korea.

(Continued)

*Primary Examiner* — Arnel C Lavarias
(74) *Attorney, Agent, or Firm* — Kurt Rauschenbach; Rauschenbach Patent Law Group, LLP (57) ABSTRACT

An optical imaging system with microlens array with integral structure includes a microlens array having a back surface for depositing sample material to be imaged and one or more microlenses on a front surface. At least one of the one or more microlenses are aligned to the deposited sample material. A plate is attached to the microlens array. A microscope objective is positioned proximate to the plurality of microlenses.

30 Claims, 9 Drawing Sheets

(52) U.S. Cl.
CPC ....... *G01N 21/6452* (2013.01); *G02B 3/0056* (2013.01); *G02B 21/06* (2013.01); *G02B 21/16* (2013.01); *G02B 21/34* (2013.01); *B01L 2300/0654* (2013.01); *B01L 2300/0822* (2013.01); *G01N 2021/6439* (2013.01); *G01N 2021/6478* (2013.01); *G01N 2021/6482* (2013.01)

(58) Field of Classification Search
USPC ....... 359/396, 397, 398, 619, 620, 621, 622; 356/244, 246; 73/863; 435/287.1, 288.3, 435/288.4, 288.7; 436/46, 164, 172
See application file for complete search history.

(56) References Cited

U.S. PATENT DOCUMENTS

| | | |
|---|---|---|
| 2004/0027707 A1 | 2/2004 | Legrand et al. |
| 2009/0136982 A1 | 5/2009 | Tang et al. |
| 2010/0021039 A1 | 1/2010 | Ortyn et al. |
| 2011/0122498 A1 | 5/2011 | Liau |
| 2011/0222051 A1 | 9/2011 | Heng |
| 2012/0061554 A1 | 3/2012 | Cui et al. |
| 2016/0320629 A1* | 11/2016 | Leonberger .......... G02B 3/0056 |

OTHER PUBLICATIONS

"Notification of Transmittal of the International Search Report and the Written Opinion of the International Searching Authority, or the Declaration" for International Patent Application No. PCT/US2016/030038, dated Aug. 9, 2016, 17 pages, International Searching Authority, Korean Intellectual Property Office, Daejeon, Republic of Korea.

"Notification Concerning Transmittal of International Preliminary Report of Patentability (Chapter I of the Patent Cooperation Treaty)", for International application No. PCT/US2016/030038, dated Nov. 16, 2017, 13 Pages, International Bureau of WIPO, Geneva, Switzerland.

\* cited by examiner

OPTICAL IMAGING SYSTEMS WITH MICROLENS ARRAY WITH INTEGRAL STRUCTURE

The section headings used herein are for organizational purposes only and should not be construed as limiting the subject matter described in the present application in any way.

CROSS REFERENCE TO RELATED APPLICATION

The present application is a non-provisional application of U.S. Provisional Patent Application No. 62/155,603 entitled "Optical Imaging Systems with Microlens Array with Integral Structure" filed on May 1, 2015. The entire contents of U.S. Provisional Patent Application No. 62/155,603 are herein incorporated by reference.

INTRODUCTION

High-resolution optical imaging has become an essential tool for investigating a wide variety of biological molecules, pathways, and dynamics in living cells and tissues. One benefit of optical imaging is that it is compatible with cells maintained in culture and enables minimally invasive observation over a wide range of timescales. The spatial resolution that can be achieved with an optical imaging system is an important metric. In a standard optical imaging system, spatial resolution is limited by the diffraction-limited focal spot size in the image plane of the optical system used for imaging. This finite spot size governs the minimum distance at which two points can be distinguished. This distance is known in the art as the "diffraction limit" of optical imaging systems.

Prior art optical microscopy techniques can readily resolve a variety of features in isolated cells and tissues, such as the nucleus, mitochondria, and Golgi complex. However, the limited spatial resolution of many optical systems limits the ability of these systems to image important elements, such as synaptic vesicles and ribosomes. In addition, the limited spatial resolution of many optical systems limits their ability to track molecular interactions because the feature size is smaller than the resolution limits. Thus, there has been considerable recent research interest in extending the resolution power of optical microscopy beyond the conventional diffraction limit of prior art optical systems. Techniques based on fluorescence imaging of biological samples are generally sophisticated and specialized. These systems include scanning near field, stochastic reconstruction, stimulated-emission depletion, and structured illumination systems. Super resolution of 100 nm or better have been reported using these prior art systems.

Solid immersion lenses (SIL) have been proposed as an alternative to the complex fluorescence imaging approaches. Solid immersion lenses use hemispherical lenses of a high-index glass to effectively shorten the observation wavelength of the imaging system. Solid immersion lenses are similar in principle to the well-known liquid immersion lens concepts used in microscopy. However, solid immersion lenses have the potential for a simpler and more general adaptation to conventional light microscopes.

BRIEF DESCRIPTION OF THE DRAWINGS

The present teaching, in accordance with preferred and exemplary embodiments, together with further advantages thereof, is more particularly described in the following detailed description, taken in conjunction with the accompanying drawings. The person skilled in the art will understand that the drawings, described below, are for illustration purposes only. The drawings are not necessarily to scale, emphasis instead generally being placed upon illustrating principles of the teaching. The drawings are not intended to limit the scope of the Applicant's teaching in any way.

DESCRIPTION OF VARIOUS EMBODIMENTS

The present teaching will now be described in more detail with reference to exemplary embodiments thereof as shown in the accompanying drawings. While the present teachings are described in conjunction with various embodiments and examples, it is not intended that the present teachings be limited to such embodiments. On the contrary, the present teachings encompass various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teachings may be performed in any order and/or simultaneously as long as the teaching remains operable. Furthermore, it should be understood that the apparatus and methods of the present teachings can include any number or all of the described embodiments as long as the teaching remains operable.

Integrated microlens array technology that combines techniques of micro-imaging via solid immersion lenses with various micro-fabrication techniques is an emerging technology. See, for example, U.S. Pat. No. 8,325,420, entitled "Annular Solid Immersion Lenses and Methods of Making Them". One limitation of prior art solid immersion lenses is the difficulty of handling small single-element high-index spherical lenses. Another limitation of prior art solid immersion lenses is the difficulty of maintaining contact with the samples. One aspect of the present teaching is the use of micro-lens arrays in various structures instead of conventional single-element lenses. The use of micro-lens array technology greatly simplifies integration with biological and other types of imaging systems.

One aspect of the present teaching relates to integrating a microlens array into a wide range of imaging systems and devices, which enables significantly improved imaging resolutions of biological and other samples. Also, the performance of such integrated microlens arrays can be much more cost effective compared with prior art devices, such as "super resolution microscopes." Furthermore, the present teaching supports a significantly superior resolution of ~4 nm with only a very small incremental cost compared to prior art, low cost microscopes that provide ~250 nm resolution.

Another aspect of the present teaching is combining techniques of solid immersion lenses and fluorescence microscopy to achieve spatial resolution previously not possible with optical imaging. In particular, the methods and apparatus of the present teaching have demonstrated spatial resolution as small as 4 nm with microspheres, mitochondria, and chromatin fibers. The solid-immersion microscopy of the present teaching, using traditional microscope systems and also using super-resolution imaging systems, provides a means for achieving higher resolution beyond the conventional diffraction limit, compared with prior art optical systems.

Another aspect of the present teaching relates to a means for integrating a microlens array into an optical imaging system in order to improve imaging resolutions. In various embodiments, one or more microlens arrays are integrated into an optical imaging system. In some embodiments, only one lenslet is used. It is understood that use of the term microlens array chip herein refers to lenslet arrays of various shapes and sizes. It should also be understood that the present teachings related to optical imaging systems with only one lenslet. Furthermore, the term microlens array refers to one- and/or two-dimensional arrays of lenslets in various configurations, shapes and spacings that may be uniform or nonuniform and comprise various array sizes and numbers of lenslets. It is also understood that where reference is made to embodiments comprising a single microlens array chip, it is intended that some embodiments may comprise multiple microlens array chips.

A wide range of microscopes can be used for the methods and apparatus of the present teaching. The microscopes may be used in various fields including biology, medicine, micro- and nano-fabrication. The microscopes may also be used in various kinds of biological, electronic and mechanical manufacturing applications. In various embodiments according to the present teaching, a microscope is imaged through air into a microlens array. In other various embodiments, a microscope is imaged via oil immersion between the microlens array and the microscope. In some embodiments, the microscope is a total-internal-reflection fluorescence (TIRF) microscope. TIRF microscopes use evanescent light to illuminate a thin region of the sample. The thin region may comprise the first one micron of sample depth, thus avoiding background from a thick sample. The thin region may also comprise other depths. TIR and TIRF microscope embodiments of the present teaching eliminate the need for preparing thin sections or reactive ion etching (RIE) of the sample.

Various methods according to the present teaching can be applied to the biological samples to enhance contrast, including using fluorescent tags, quantum dots, and nanotube probes. Tissue sections can be treated and prepared using methods commonly used in state-of-the-art optical imaging of biological samples, including fixing and staining, as well as live-culture sample preparation and testing techniques. Aspects of the present teaching that are useful for handling thin microlens array(s) can be used to attach tissue sections to the back surfaces of the microlens array chips. While many aspects of the present disclosure relate to the application of the microlens array with integral structure into biological imaging systems, it will be apparent to those skilled in the art that the technique can be applied to other imaging applications. For example, many aspects of the present disclosure can be used for inorganic molecular imaging, micro- and nano-fabrication applications (including imaging of micro- and nano-electronic and photonic device structures), and for a wide variety of scientific microscope imaging applications.

Figure 1:
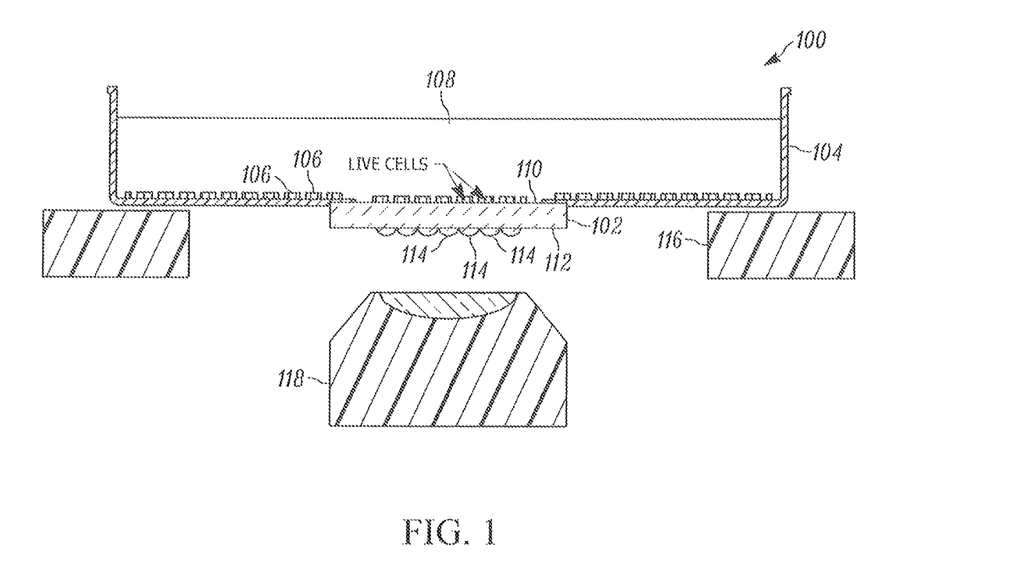
FIG. 1 illustrates an embodiment of an imaging microscope system with a microlens array chip integrated into the bottom of a sample container, according to the present teaching.

FIG. 1 illustrates an embodiment of an imaging microscope system 100 with a microlens array chip 102 integrated into a plate that may comprise the bottom of a container 104, according to the present teaching. In various embodiments the container 104 comprises a Petri dish, a specimen jar, a vial, a bottle or any other container for biological material. The plate may also comprise a microplate or any variety of microscope slide or microarray slide known in the art. In various embodiments, one or more microlens array chips 102 may be integrated. One feature of the embodiment of the imaging system illustrated in FIG. 1 is that it advantageously enables the handling of relatively thin microlens array chips 102. For example, the microlens array chips can be ~150 μm thick.

Live cells 106 can be grown in a culture medium 108 contained in the container 104. This imaging microscope system 100 allows live cells 106 to be cultured directly on the back surface 110 of the microlens array chip 102. The front surface 112 of the microlens array chip 102 comprises the array of lens structures 114. The lens structures 114 can include any number of known immersion lens structures and materials known in the art. In many embodiments, the lens structure 114 is a high index lens structure. In some embodiments, the immersion lens structure 114 comprises a hemisphere lens shape made of GaP material. The Petri dish 104 is held on a microscope stage 116. A microscope objective lens 118 is positioned to image the front surface 110 of the microlens array chip 102. This configuration allows the live cells 106 to be imaged by a high-resolution microscope.

One feature of the microlens array chip 102 mounted with the back surface 110 exposed to the culture medium 108 is that it advantageously enables simple cell culturing where the microlenses are entirely protected from exposure to the aqueous culture medium 108. As with conventional microscope slides, the live cells 106 can be fixed and stained after the culture medium 108 is drained. During microscope examination, the image resolution is greatly increased by the high-index microlens structures 114 of the microlens array chip 102. Alternatively, the live cells 106 living in the culture medium 108 can be placed directly over the objective lens 118 of an inverted microscope for live-cell examination. Live-cell imaging is often performed with fluorescence microscopy, but other microscope imaging techniques can also be used.

The embodiment illustrated in FIG. 1 also allows for a confocal laser-scanning microscope configuration. In this configuration, the microlens array chip 102 provides a smaller excitation spot of the scanning laser, which results from focusing by the high-index microlens. This small excitation spot can significantly increase the fluorescence intensity and efficiency. The small excitation spot also allows for fast scanning, which is desirable in the imaging of highly dynamic live cells. Furthermore, the high power density resulting from the strong focusing of the laser light into a small spot favors improved, multi-photon, super resolution microscopy.

Figure 2:
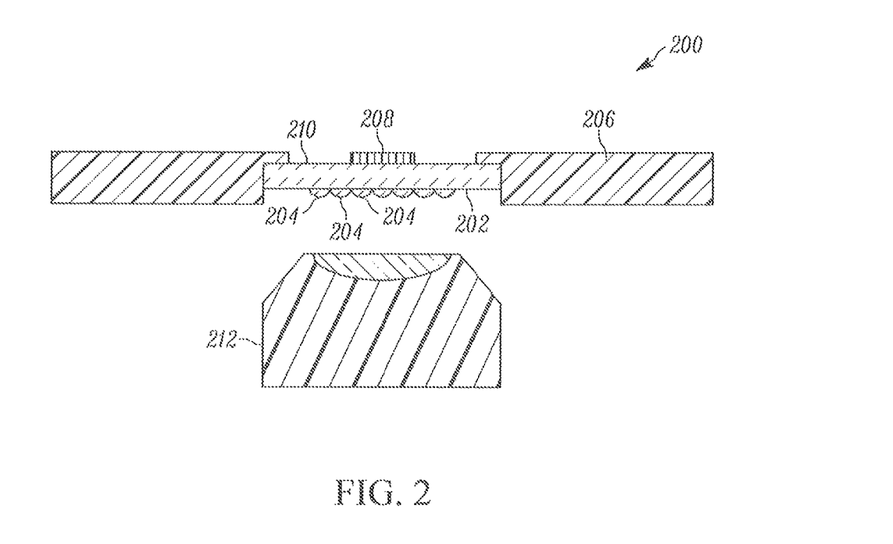
FIG. 2 illustrates an embodiment of the imaging system with microlens array with integral structure comprising a microscope slide with integrated microlens array chip, according to the present teaching.

FIG. 2 illustrates an embodiment of an imaging system 200 of the present teaching comprising an integrated microlens array chip 202 with one or more arrays of microlenses 204. The microlens array chip 202 is integrated into a plate that can be a microscope slide 206. The microscope slide 206 can be made of glass, plastic, or any other suitable material. In various embodiments, one or more microlens array chip may be integrated onto the microscope slide. The configuration illustrated in FIG. 2 is suitable for attaching a thin biological sample, such as a tissue section 208, to the back surface 210 of the microlens array chip 202 for microscope examination. In the embodiment shown in FIG. 2, the microscope slide 206 is designed to protect the microlenses 204 by mounting the microlens array chip 202 such that the top of the microlenses 204 are slightly recessed from the top of the microscope slide 206. The recess is designed so that the microscope objective lens 212 does not hit the top of the slide 206. In various embodiments, the microscope slide 206 may also comprise various sample mounting elements, such as a cytology slide, histology slide, adhesive slide, microarray slide, or other diagnostic slides known in the art.

In some embodiments of the imaging system 200, fluorescent in situ hybridization (FISH) is used. In these embodiments, the sample 208 comprises a nucleic acid such as chromosomes, DNA, RNA, or other materials that have been tagged with fluorescent probes (not shown). The sample 208 is placed on the microlens array chip 202 for microscope examination. When using FISH, the microlenses 204 of the present teaching provide higher image resolution and contrast, which allows more fluorescent probes to be imaged. One feature of the imaging system of the present teaching is that it permits fluorescent probes that are very close together (on order of a few nanometers) to be resolved as separate probes. Also, the methods and apparatus of the present teaching advantageously allows less fluorescent material to be used, thereby decreasing the amount that samples under examination are perturbed.

In other embodiments of the microlens array chip 202 integrated into a microscope slide 206, the microlens array chip 202 is integrated directly into a glass cover slip and placed over the biological sample. The sample can then be imaged from above using a microscope objective that is positioned on the opposite side of the microscope slide.

Figure 3:
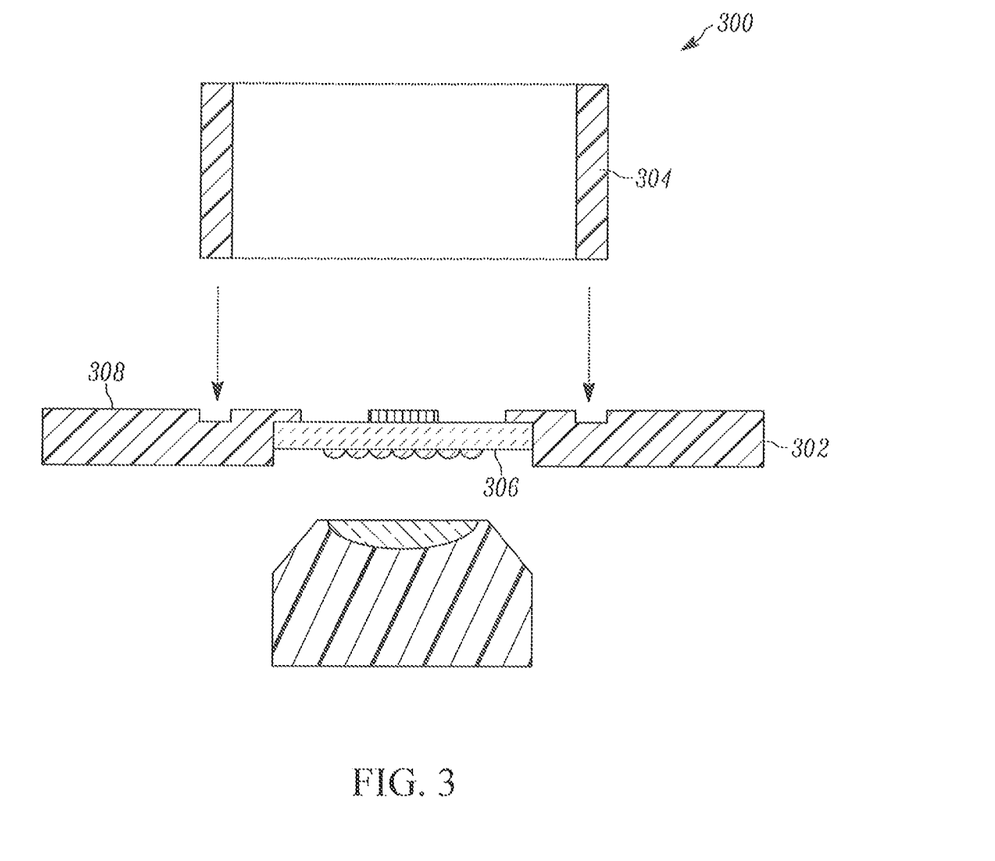
FIG. 3 illustrates an embodiment of an imaging system comprising a microscope slide including a container sidewall, according to the present teaching.

FIG. 3 illustrates an embodiment of an imaging system 300 comprising a microscope slide 302 including a container sidewall 304, according to the present teaching. In the imaging system 300, the microlens array chip 306 is integrated into the microscope slide 302. The microscope slide 302 can be designed to affix a containing side wall 304 onto the back surface 308 of the microscope slide 302, which can have one or any number of contained wells (e.g., 2, 4, 8, 16, 64, 96, etc.). This allows the use of the microscope slide 302 to generate cell cultures, similar to culture generation possible with the Petri dish 104 in the imaging microscope system 100 of FIG. 1. The microscope slide 302 can be used either for live-cell imaging or for cell fixation and staining. When used for cell staining, the containing wall 304 can eventually be removed, and the slide 302 will perform like a conventional slide with an integrated microlens array chip 306.

Figure 4A:
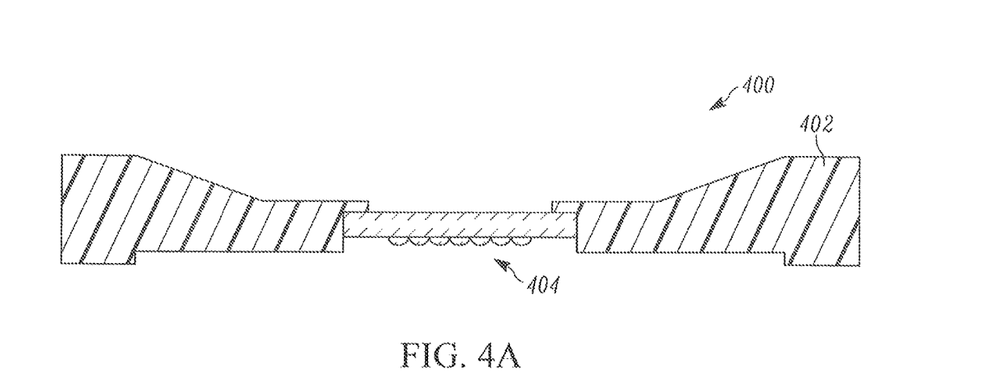
FIG. 4A illustrates an embodiment of a microscope slide including a container sidewall built into a microscope slide and an integrated microlens array, according to the present teaching.

FIG. 4A illustrates an embodiment of a microscope slide 400 including a container sidewall 402 built into a microscope slide 400 with an integrated microlens array 404, according to the present teaching. The microscope slide 400 can be on the order of 1-2 mm thick. However, this embodiment of the present teaching can be used with microscope slides 400 of any thickness.

Figure 4B:
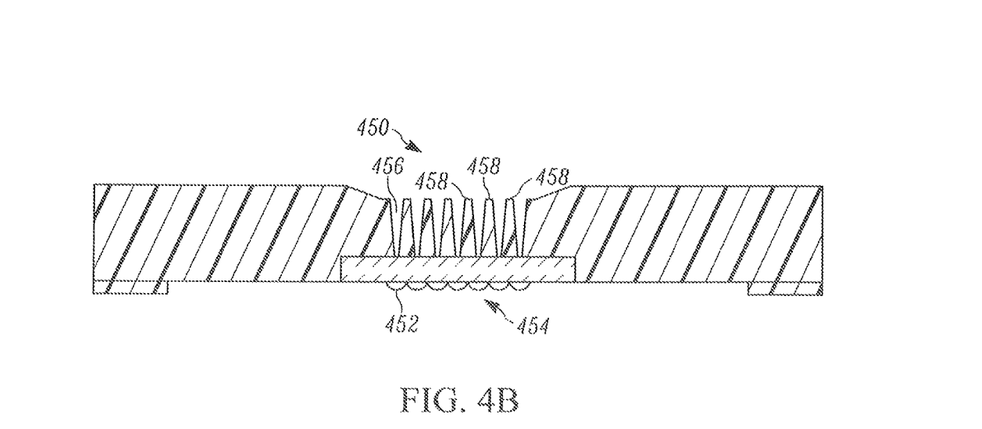
FIG. 4B illustrates an embodiment of a microscope slide, according to the present teaching, where each microlens of the microlens array with integral structure has its own containing well.

FIG. 4B illustrates an embodiment of a microscope slide 450, according to the present teaching, where each microlens 452 of the integrated microlens array 454 has its own containing well 456. A side-view of the microscope slide 450 resembles a honeycomb because each containing well 456 forms a high-aspect-ratio structure 458 that is wide at the mouth and tapers to the field-of-view of the microlens on the bottom. The containing wells 456 are built into the microscope slide 450 comprising the integrated microlens array, according to the present teaching. Each containing well 456 comprises a high-aspect-ratio structure 458 that isolates a particular microlens. In some other embodiments (not shown), at least one containing well 456 isolates more than one microlens.

One feature of the container wells 456 of the present teaching is that each cell or group of cells can be isolated from other cells/groups of cells in its own tapered well. Isolating each cell or group of cells in tapered wells according to the high-aspect ratio structure 458 results in a highly efficient cell culture and subsequent array screening, because the cells are channeled to the field-of-view of the microlens array 454. Consequently, the microscope slide 450 can facilitate high-volume screening with minimum reagent use.

Figure 5:
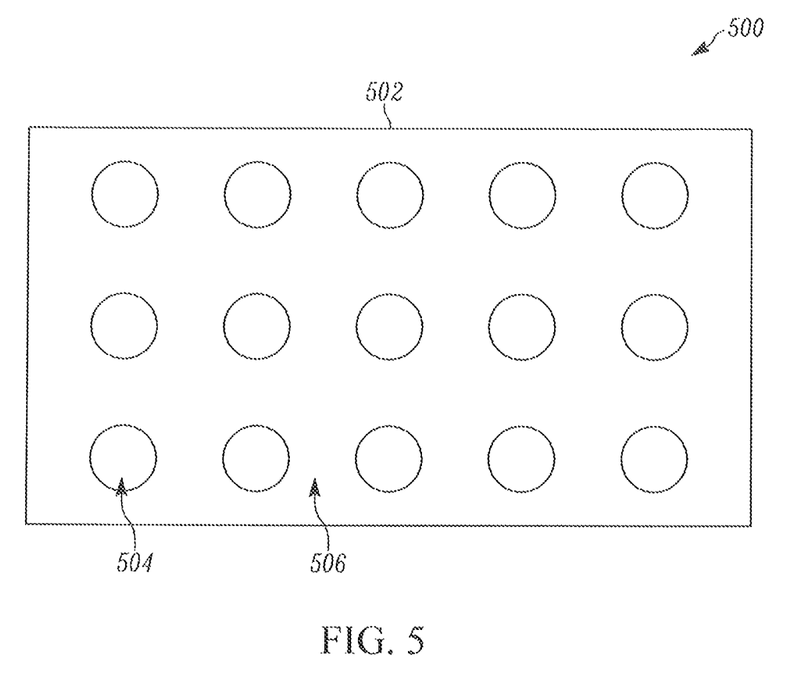
FIG. 5 illustrates a backside-patterned coated microlens array, according to the present teaching.

FIG. 5 illustrates a microlens array 500 with a backside-patterned coating, according to the present teaching. The microlenses are not visible in FIG. 5 because they are positioned on the front surface of the integrated microlens array 500, opposite to the back surface coating 502. Backside-patterned coatings 502 can be used for various reasons, such as to improve sample preparation, for integration mechanics, or to improve the imaging of the system. The backside-patterned coatings can enable efficient cell culture and subsequent screening with minimal use of expensive reagents. For example, in some embodiments, the purpose of the backside-patterned coatings 502 is to seal against leakage of a culture medium. In other embodiments, the purpose of the backside-patterned coatings 502 is to protect against leakage of epoxy.

The backside-patterned coating 502 is patterned for selective cell adhesion to circular regions 504. In various embodiments, other shaped regions are used. In some embodiments, the backside-patterned coating 502 has a diameter that corresponds to the field-of-view of the microlenses. For example, the backside-patterned coating 502 can have a 50-micron diameter that corresponds to a 50-micron field-of-view.

In one embodiment, the circular region 504 includes a hydrophilic material that attracts cells to the circular regions 504. The surrounding area 506 may be coated with a hydrophobic material that helps usher the cells away from the surrounding area.

One feature of the microlens array with integral structure chips of the present teaching is that the back surface can be patterned using various types of microlithography techniques that are commonly used in the semiconductor and micro-fabrication industries. Such microlithography techniques are highly refined, and the equipment is commonly available. Lithography and other micro-fabrication techniques can be used to construct various electrical, optical, and mechanical elements on both sides of the microlens array chip. The back surface of the microlens array 500 can also be attached to different elements, including mechanical, biological, and electrical elements that add functionality to the microlens array with integral structure chip.

Figure 6A:
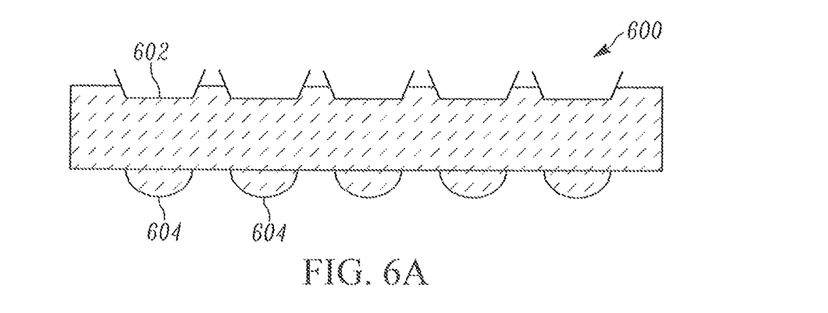
FIG. 6A illustrates a side-view of an annular solid-immersion lenslet array that includes micro-fabricated wells on the back surface of the chip, according to the present teaching.
Figure 6B:
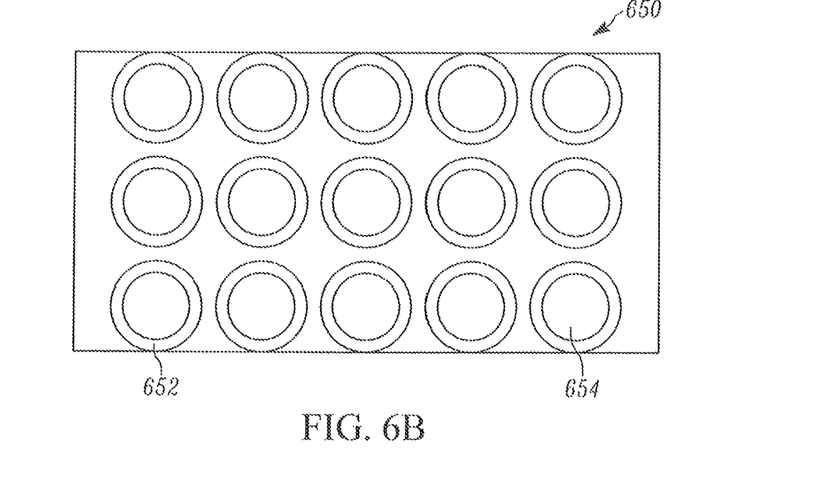
FIG. 6B illustrates a top-view of the back surface of a backside-patterned annular solid-immersion lenslet array, according to the present teaching.
Figure 6C:
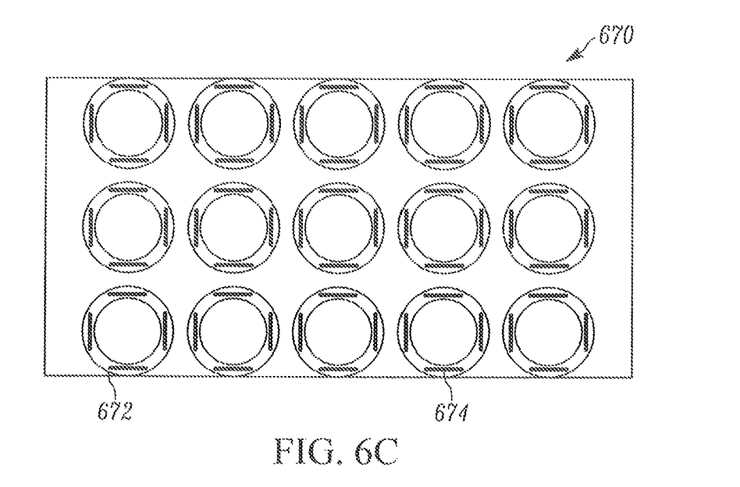
FIG. 6C illustrates a top-view of the back surface of a backside-patterned microlens array with integrated electrodes with addressing wires, according to the present teaching.

FIGS. 6A-C illustrate various views of a backside-patterned microlens array 600. The implementation of micro-fabricated semiconductor solid immersion lenses in the form of arrays is referred to herein as annular solid-immersion lenslet array (ASILA). FIG. 6A illustrates a side-view of an annular solid-immersion lenslet array that includes micro-fabricated wells 602 on the back surface of the array 600. The micro-fabricated wells 602 are positioned over the lenslets 604, and may be arranged in a regular pattern. The micro-fabricated array of wells 602 facilitates various methods of systematic testing and variations. For example, the micro-fabricated array of wells 602 is suitable for high-throughput drug screening applications.

FIG. 6B illustrates a top-view of the back surface of a backside-patterned annular solid-immersion lenslet array 650, according to the present teaching. The backside-patterned annular solid-immersion lenslet array 650 shows annular electrodes 652 formed into an array 650. Circular wells 654 are patterned into the solid-immersion lenslet array 650. The wells 654 are positioned over the lenslets (not visible in the diagram of FIG. 6B). The array 650 may be divided into sub-sections that allow controlled electric field patterns to be applied to the biological samples.

FIG. 6C illustrates a top-view of the back surface of a backside-patterned microlens array 670 with integrated electrodes 672 with addressing wires, according to the present teaching. The addressing wires are used to connect the electrodes 672 to control various electronics.

Figure 7A:
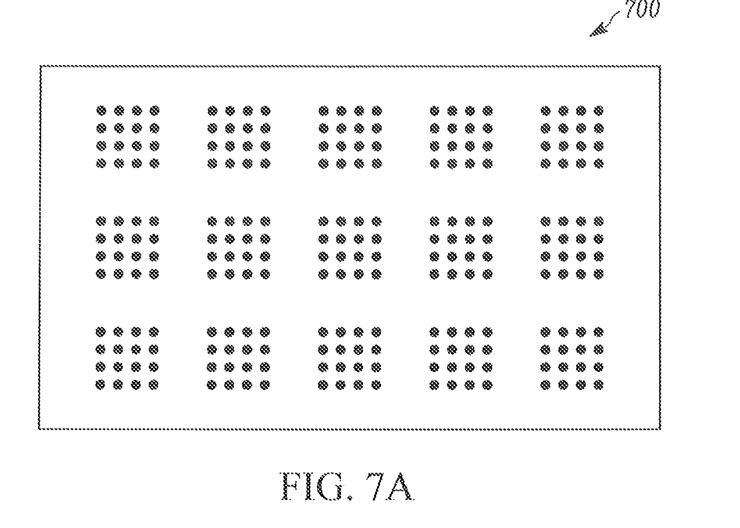
FIG. 7A illustrates a top-view of a circuit chip for a microlens array, according to the present teaching.

FIG. 7A illustrates a top-view of a circuit chip 700 for a microlens array, according to the present teaching. The circuit chip 700 is used to provide control electronics to the annular solid-immersion lenslet array chip.

Figure 7B:
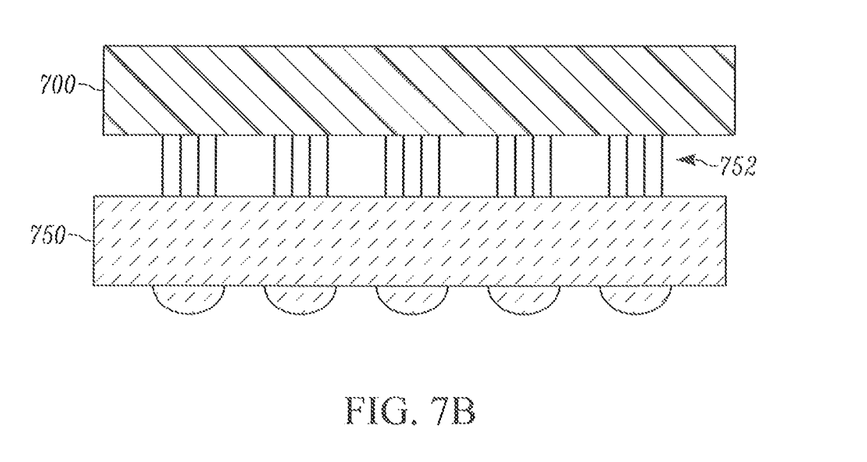
FIG. 7B illustrates a side-view of a circuit chip and a microlens array, according to the present teaching.

FIG. 7B illustrates a side-view of a combination of the circuit chip 700 and a microlens array 750, according to the present teaching. More specifically, FIG. 7B illustrates a side-view of the circuit chip 700 that is connected to an annular solid-immersion lenslet array chip 750 using probes 752. The position of the probes 752, together with the position of the addressing wires (see FIG. 6C showing the top-view of the back surface of a backside-patterned microlens array with integrated electrodes with addressing wires), provides an applied control field for pin-point stimulation of the biological samples. In some embodiments, the integrated electrodes provide control fields that stimulate the cells through the microlens array while under high-resolution microscope examination.

Figure 8:
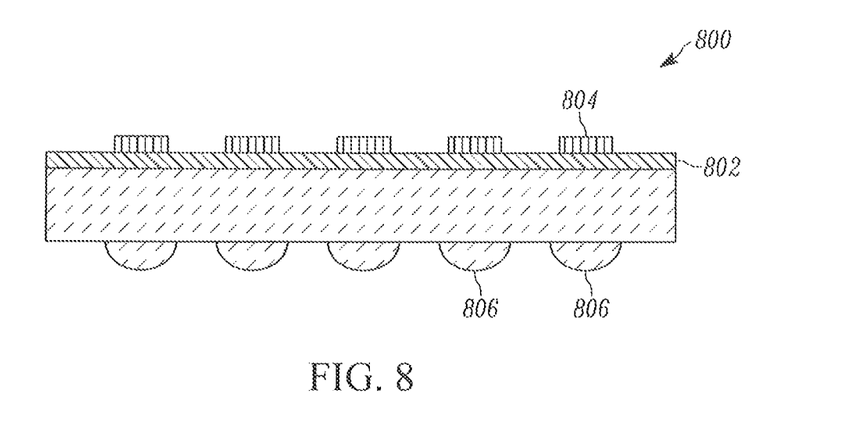
FIG. 8 illustrates an embodiment of a microlens array chip comprising an optical waveguide integrated on the back surface, according to the present teaching.

FIG. 8 illustrates an embodiment of a microlens array chip 800 comprising an integrated optical waveguide 802 on the back surface, according to the present teaching. The optical waveguide 802 may be constructed using various micro-fabrication methods known in the art. The optical waveguide 802 may be deposited by various deposition techniques, or may be epitaxially grown. Biological samples 804 may be place on the waveguide 802 for sampling and imaging through the microlenses 806.

In some embodiments, the optical waveguides 802 are used for illuminating the biological samples 804. The integrated optical waveguides 802 can be highly efficient and can provide high brightness, since the light in the optical waveguides bounces back-and-forth many times, which increases the probability of scattering for imaging.

In some methods of operations, standing-wave patterns for structured illumination can be established in the waveguides by introducing counter propagation light beams into the waveguide. The high-index microlens material affords smaller packets of light in the standing wave, which can greatly increase the resolving power of the optical system.

Figure 9A:
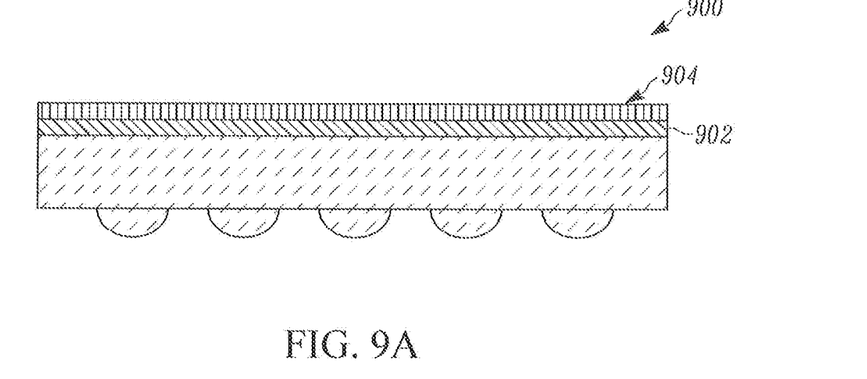
FIG. 9A illustrates an embodiment of a microlens array chip comprising fluorescent materials deposited following a biological sample deposited on the back surface of the chip, according to the present teaching.
Figure 9B:
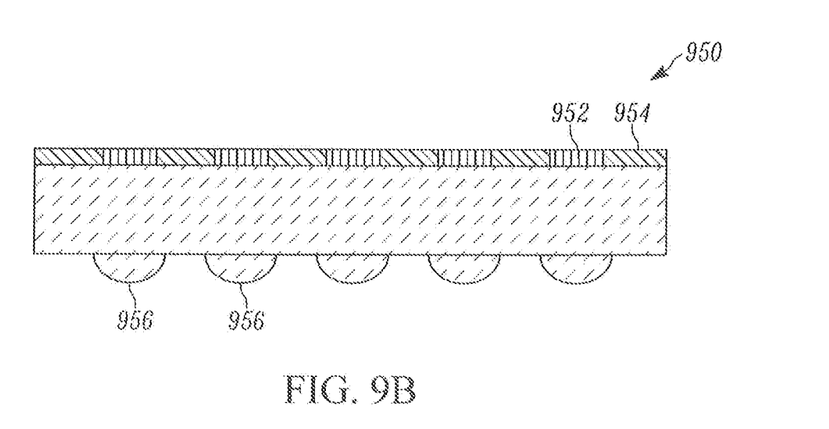
FIG. 9B illustrates an embodiment of a microlens array chip comprising fluorescent materials deposited on the back surface of the chip so as to surround a biological sample, according to the present teaching.

FIGS. 9A-B illustrate a microlens array chip, according to the present teaching, including biological material covered by fluorescent material on the back surface of the microlens array chip. FIG. 9A illustrates an embodiment of the microlens array chip 900 in which a biological sample material 902 is applied across the microlens array chip 900, and then a fluorescent material 904 is applied over the biological material 902.

FIG. 9B illustrates an embodiment of the microlens array chip 950 wherein the fluorescent material 954 is applied to fill in the areas surrounding the biological or nanotechnological sample material 952. In this embodiment, the biological sample 952 is placed over the microlens 956. One skilled in the art will appreciate that there are numerous other configurations where fluorescent material is positioned over biological material and aligned with microlenses. For example, in various embodiments, the fluorescent material 954 can be deposited in the form of fluorescent microspheres or quantum dots. Note that samples 952 and 1004 (FIG. 10) are very small objects like nanotubes, virus, or bacteria. These may or may not have fluorescence tagging, and the present teaching provides non-coherent passive illumination, or decoration (especially with quantum dots) to show their outline. Coating 1002 (FIG. 10) further provides high-index coating to increase the index contrast (i.e., visibility).

The fluorescent material 904 deposited over the biological or nanotechnological sample material 902 is essentially an integrated illumination light source. The applied fluorescent material provides efficient illumination directly on the biological sample material 902. One feature of the fluorescent material is that it is non-coherent, and thus does not have the dominant coherent interference effects that are often detrimental to high-resolution microscopy. Yet another feature of the fluorescent material 954 is that it can be used to decorate the sample for more pronounced delineation.

Figure 10:
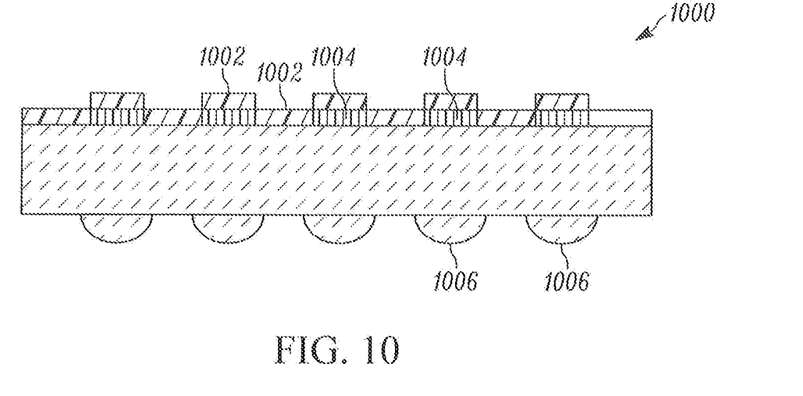
FIG. 10 illustrates an embodiment of a fabricated microlens array chip of the present teaching comprising an optical coating deposited on the back surface of the microlens array chip.

FIG. 10 illustrates an embodiment of a fabricated microlens array chip 1000 of the present teaching comprising an optical coating 1002 deposited on the back surface of the microlens array chip 1000. The microlens array chip 1000 has a pattern of biological materials 1004 arranged on the back surface of the microlens array chip that is aligned over the microlenses 1006.

In the embodiment of the fabricated microlens array chip 1000 illustrated in FIG. 10, biological or nanotechnological materials 1004 are first deposited over a microlens. An optical coating 1002 is then deposited over the entire surface so that an optical coating material is on top of the biological sample and also surrounding the biological sample 1004. One skilled in the art will appreciate that there are numerous techniques known in the art for patterning the biological material 1004, and for subsequently coating the surface of the chip 1000.

In some specific embodiments, the optical material 1002 comprises silicon or titanium oxide. The optical material can be chosen to provide a particular optical effect, such as providing an appropriate optical refractive index for the imaging system, or for providing some kind of filtering function. Some optical materials, such as silicon, provide a high refractive index that can significantly improve the image contrast. The optical material may be chosen for a specific optical effect given the particular optical properties of the biological sample, such as refractive index, optical transparency, or other. In some embodiments, the deposited material is chosen to have a waveguiding effect that increases illumination.

In various embodiments of the present teaching, including those shown in FIGS. 1-10, a thin material may reside between the biological sample and the microlens array. The thin material may comprise glass, adhesive, or other material. The thin material may be used to pattern or position the sample, to affix the sample, or to create a desired optical imaging distance or effect when the sample is imaged by the microlens array. Note that samples generally have some thickness, and light originated from points from within the sample travel through the material to reach the backside surface of the microlens array. In various embodiments, distances between the center of curvature of the lenslets in the microlens array and the sample are chosen to provide a desired resolution. The thickness and optical refractive properties of the thin material may be chosen to achieve a desired resolution.

As described earlier, the microlens array chips of the current teaching are not limited to biological imaging applications. Other applications include imaging of micro- and nano-structured systems such as mechanical systems, electronic systems or hybrid systems. Devices under test may include micro-mechanical mirrors or MEMs devices, electronic integrated circuits, optical circuits and electro-optic circuits. Applications also include determining surface features, such as roughness, in both large scale and small scale elements, such as optical, mechanical or electronic elements. The systems may provide images of the elements under test, or provide measurements of particular feature sizes, dimensions and/or shapes.

Figure 11:
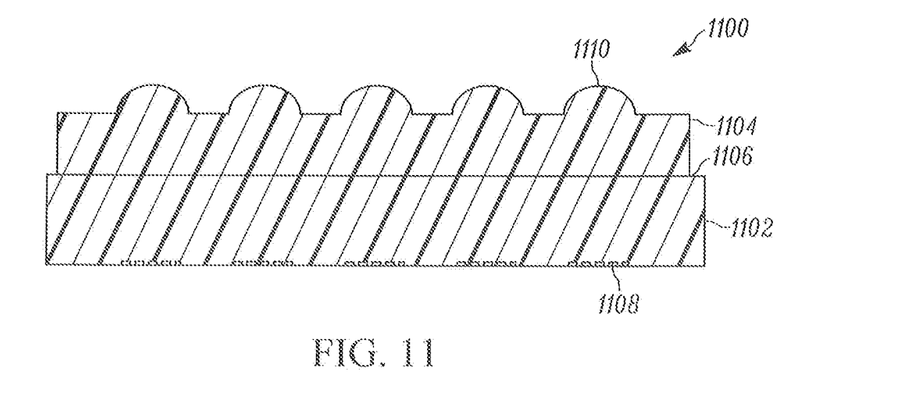
FIG. 11 illustrates an embodiment of an imaging system for high-resolution imaging and measurement of an integrated circuit using microlens array with integral structures according to the present teaching.

FIG. 11 illustrates an embodiment of an imaging system 1100 for nano-scale-feature-measurement for an integrated circuit chip 1102. The integrated circuit chip 1102 is bonded to a microlens array chip 1104. In various embodiments, the microlens array chip 1104 is made from various substrates comprising Si, Ge, GaAs, GaP, or other III-V, II-VI, and IV-VI semiconductors. The microlens array chip 1104 is wafer bonded to the integrated circuit chip 1102 at the interface 1106 between the microlens array chip 1104 and the integrated circuit chip 1102 using various wafer bonding techniques known in the art. In some embodiments, one or more test circuits 1108 on the surface of the integrated circuit is positioned at the center of curvature of one or more lenslets 1110.

In some embodiments of the imaging system 1100 for nano-scale-feature-measurement for an integrated circuit chip 1102, the combined thickness of the two chips is chosen to match a radius of curvature of one or more of the lenslets 1110. Also, in some embodiments of the imaging system 1100, there is a sufficiently small gap between the microlens array chip 1004 and the integrated circuit chip 1102 that is on order of 100 nm which is chosen to facilitate evanescent wave tunneling. Also, in some embodiments of the imaging system 1100, the field of view is adjustable by sliding the microlens array chip 1004 relative to the integrated circuit chip 1102.

Equivalents

While the Applicant's teaching is described in conjunction with various embodiments, it is not intended that the Applicant's teaching be limited to such embodiments. On the contrary, the Applicant's teaching encompasses various alternatives, modifications, and equivalents, as will be appreciated by those of skill in the art, which may be made therein without departing from the spirit and scope of the teaching.

What is claimed is:

1. An optical imaging system having a microlens array with integral structure, the optical imaging system comprising:
   a) the microlens array comprising a back surface for depositing sample material to be imaged and one or more microlenses on a front surface, wherein at least one of the one or more microlenses are aligned to the deposited sample material;
   b) a plate attached to the microlens array;
   c) a microscope objective positioned proximate to the one or more microlenses; and
   d) a fluid container attached to the plate so that the back surface of the microlens array can be immersed in a fluid in the fluid container.

2. The optical imaging system with the microlens array with integral structure of claim 1 wherein the fluid container is positioned in recesses in the plate.

3. The optical imaging system with the microlens array with integral structure of claim 1 wherein the fluid container comprises a Petri dish.

4. The optical imaging system with the microlens array with integral structure of claim 1 wherein the fluid container is selected from the group consisting of a specimen jar, a vial and a bottle or other container for biological material.

5. The optical imaging system with the microlens array with integral structure of claim 1 wherein the plate comprises a microscope slide.

6. The optical imaging system with the microlens array with integral structure of claim 1 wherein the plate comprises a microscope slide.

7. The optical imaging system with the microlens array with integral structure of claim 1 wherein the plate comprises a microarray slide.

8. The optical imaging system with the microlens array with integral structure of claim 1 wherein the plate defines a plurality of wells, wherein each of the plurality of wells is positioned over a respective one of the one or more microlenses.

9. The optical imaging system with the microlens array with integral structure of claim 8 wherein at least one well in the plurality of wells is tapered proximate to the respective one of the one or more microlenses.

10. The optical imaging system with the microlens array with integral structure of claim 1 wherein the microlens array comprises integrated electrodes with addressing wires.

11. The optical imaging system with the microlens array with integral structure of claim 10 wherein the integrated electrodes are formed in an annular shape.

12. The optical imaging system with the microlens array with integral structure of claim 10 wherein the integrated electrodes comprise sections that allow controlled electric field patterns.

13. The optical imaging system with the microlens array with integral structure of claim 10 wherein the integrated electrodes comprise sections that apply a control field for pin-point stimulation.

14. The optical imaging system with the microlens array with integral structure of claim 1 wherein the microlens array comprises an optical waveguide positioned proximate to the back surface.

15. The optical imaging system with the microlens array with integral structure of claim 14 wherein the optical waveguide is dimensioned to achieve structured illumination.

16. The optical imaging system with the microlens array with integral structure of claim 1 wherein the microlens array comprises fluorescent material positioned proximate to the back surface.

17. The optical imaging system with the microlens array with integral structure of claim 16 wherein the fluorescent material is positioned over the deposited sample material.

18. The optical imaging system with the microlens array with integral structure of claim 16 wherein the fluorescent material comprises fluorescent microspheres.

19. The optical imaging system with the microlens array with integral structure of claim 16 wherein the fluorescent material comprises quantum dots.

20. The optical imaging system with the microlens array with integral structure of claim 1 wherein the microlens array comprises an optical coating proximate to the back surface.

21. The optical imaging system with the microlens array with integral structure of claim 20 wherein the optical coating is positioned over the deposited sample material.

22. A method of optical imaging, the method comprising:
   a) providing a microlens array that includes a back surface for depositing sample material to be imaged and one or more microlenses on a front surface;
   b) aligning at least one of the one or more microlenses to the deposited sample material;
   c) attaching a plate to the microlens array;
   d) positioning a microscope objective proximate to the one or more microlenses; and
   e) immersing the back surface of the microlens array in a fluid.

23. The method of claim 22 further comprising positioning a plurality of wells in the plate over a respective one of the one or more microlenses.

24. The method of claim 22 further comprising individually addressing integrated electrodes in the microlens array.

25. The method of claim 22 further comprising individually addressing integrated electrodes in the microlens array to achieve a particular electric field pattern.

26. The method of claim 22 further comprising individually addressing integrated electrodes in the microlens array to apply a control field for pin-point stimulation.

27. The method of claim 22 further comprising providing structured illumination with an optical waveguide in the microlens array.

28. The method of claim 22 further comprising positioning fluorescent material proximate to the back surface.

29. The method of claim 28 wherein the fluorescent material comprises fluorescent microspheres.

30. The method of claim 28 wherein the fluorescent material comprises fluorescent quantum dots.

\* \* \* \* \*